(12) United States Patent
Miyake (10) Patent No.: US 8,736,677 B2
(45) Date of Patent: May 27, 2014

(54) INSPECTION SYSTEM

(75) Inventor: Atsushi Miyake, Nishinomiya (JP)

(73) Assignee: KDE Corporation, Osaka (JP)

( * ) Notice: Subject to any disclaimer, the term of this patent is extended or adjusted under 35 U.S.C. 154(b) by 580 days.

(21) Appl. No.: 13/057,992

(22) PCT Filed: Aug. 7, 2008

(86) PCT No.: PCT/JP2008/064252
§ 371 (c)(1),
(2), (4) Date: Feb. 7, 2011

(87) PCT Pub. No.: WO2010/016137
PCT Pub. Date: Feb. 11, 2010

(65) Prior Publication Data
US 2011/0141270 A1    Jun. 16, 2011

(51) Int. Cl.
*H04N 7/18* (2006.01)

(52) U.S. Cl.
CPC ..................................... *H04N 7/18* (2013.01)
USPC .......................................................... 348/125

(58) Field of Classification Search
CPC ........................................................ H04N 7/18
USPC .......................................................... 348/125
See application file for complete search history.

(56) References Cited

U.S. PATENT DOCUMENTS

| | | | | |
|---|---|---|---|---|
| 5,917,934 A | * | 6/1999 | Chiu et al. | 382/149 |
| 6,061,086 A | * | 5/2000 | Reimer et al. | 348/125 |
| 6,064,759 A | * | 5/2000 | Buckley et al. | 382/154 |
| 6,748,110 B1 | * | 6/2004 | Wallack | 382/173 |
| 6,778,694 B1 | * | 8/2004 | Alexandre | 382/141 |
| 6,987,875 B1 | * | 1/2006 | Wallack | 382/146 |
| 7,162,073 B1 | * | 1/2007 | Akgul et al. | 382/149 |
| 7,619,668 B2 | * | 11/2009 | Saka et al. | 348/251 |
| 7,769,223 B2 | * | 8/2010 | Shinohara et al. | 382/141 |

(Continued)

FOREIGN PATENT DOCUMENTS

| | | |
|---|---|---|
| JP | 08-247954 A | 9/1996 |
| JP | 09-089603 A | 4/1997 |

(Continued)

OTHER PUBLICATIONS

ISA Japanese Patent Office, International Search Report of PCT/JP2008/064252, Sep. 2, 2008, 4 pages.

*Primary Examiner* — Y Lee
*Assistant Examiner* — Irfan Habib
(74) *Attorney, Agent, or Firm* — Alleman Hall McCoy Russell & Tuttle LLP (57) ABSTRACT

An inspection system is provided that can calculate highly accurate data for inspection having a high S/N ratio with high freedom. In order to attain this, an imaging timing is adjusted to synchronize a time for a projected image of an object to move by "m" pixels ("m" is an integer number greater than or equal to 1) in the X-axis direction on imaging elements, with an imaging time interval, and partial image data imaged at the identical inspection position on the object is specified from each unit of two-dimensional image data based on the object appearing deviated by "m" pixels in the X-axis direction in each unit of the two-dimensional image data imaged at each of the imaging timings, and data for inspection in which a noise reducing processing is conducted at the inspection position is produced based on each section of the partial image data.

4 Claims, 10 Drawing Sheets

(56) References Cited

U.S. PATENT DOCUMENTS

| | | | |
|---|---|---|---|
| 7,796,801 B2* | 9/2010 | Kitamura et al. | 382/141 |
| 7,847,819 B2* | 12/2010 | Oka | 348/125 |
| 8,045,785 B2* | 10/2011 | Kitamura et al. | 382/141 |
| 8,164,625 B2* | 4/2012 | Klawunder | 348/125 |
| 2005/0213807 A1* | 9/2005 | Wasserman | 382/152 |
| 2006/0007313 A1* | 1/2006 | Oka | 348/180 |
| 2006/0088202 A1* | 4/2006 | Venkatachalam | 382/152 |
| 2006/0098190 A1* | 5/2006 | Miyake et al. | 356/239.1 |
| 2007/0012865 A1* | 1/2007 | Katzir et al. | 250/208.1 |
| 2007/0273828 A1* | 11/2007 | Polland et al. | 351/204 |
| 2008/0297695 A1* | 12/2008 | Sekiguchi et al. | 349/65 |

FOREIGN PATENT DOCUMENTS

| | | |
|---|---|---|
| JP | 2000-352557 A | 12/2000 |
| JP | 2004-251878 A | 9/2004 |
| JP | 2008-501960 A | 1/2008 |

* cited by examiner

Fig. 14

INSPECTION SYSTEM

FIELD OF THE ART

This invention relates to an inspection system to extract and inspect a distortion existing inside of a transparent platy body such as a glass plate or a flaw or a foreign material (hereinafter also collectively called as a defect) existing on a surface of a mirror-finished platy body based on an imaged image.

BACKGROUND ART

A CCD is often utilized as a line sensor for this kind of the inspection system. The line sensor has an arrangement wherein multiple photodiodes are arranged in line and CCDs are arranged in parallel to correspond to each of the photo diodes. Then, electric charge generated due to exposure of the photodiode is charged to the CCD and the charged electric charge is read out respectively so that a line of the image data is produced.

Since it is not possible for this kind of line sensor to conduct a next exposure until an electric charge charged to the CCD is read out and reset, it is relatively difficult to significantly shorten an interval of exposure, namely, an imaging interval, if a reset time is also included. However, by conversely utilizing the property that an electric charge is stored in succession until the CCD is reset, recently a line sensor has been developed that employs a TDI (Time Delay Integration) method which can conduct sensing at high speed and high accuracy.

The TDI method is to synchronize a moving speed of an object projected to the CCD in a direction of a column with a timing of transferring the electric charge in a vertical direction and to conduct an integral exposure by a number of vertical steps (for example, "M" steps) by utilizing a property that the electric charge is vertically transferred by a unit of a column at a time of reading out the electric charge, where the CCD is arranged in two-dimensions, so that a sensitivity by "M" times of an ordinary linear image sensor can be realized. In short, the identical position of the object is imaged at "M" times and all of the imaged images are overlapped so as to improve the sensitivity.

Patent document 1: Japan Patent Laid-open number 2004-251878

DISCLOSURE OF THE INVENTION

Problems to be Solved by the Invention

With this TDI method, however, the electric charge of the CCD at each imaging timing is simply integrated. Accordingly, the above-mentioned TDI linear image sensor cannot be used for the purpose of constructing useful image data with an improved S/N ratio by providing some sort of calculation on an electric charge amount at each of the imaging timings followed by integrating the calculation results. In addition, there is also a problem that the CCD used for TDI is expensive.

For example, with a defect detecting device shown in the patent document 1 that has been applied and patented by the present claimed inventor, Moire fringes are formed on the image data by making use of a grid pattern and a defect is detected based on a disorder of a sine wave appearing on the Moire fringes. In this case, the disorder of the sine wave is detected by producing the data for inspection by providing a predetermined calculation of an output value of each of the imaging elements such as the CCD. In order to improve the S/N ratio for this defect detecting device, it is useful to integrate by multiple times the output value of each of the imaging elements on which the predetermined calculation is provided, however, it is difficult to use the TDI linear image sensor for this purpose.

The present claimed invention intends to solve all of the problems and to provide an inspection system that can calculate the data for inspection having a high S/N ratio and high accuracy with high freedom.

Means to Solve the Problems

More specifically, an inspection system in accordance with this invention comprises an imaging device having multiple imaging elements arranged in two-dimensions along an X-axis and a Y-axis which are two virtual orthogonal axes, an imaging control section that receives a light intensity signal from all or a part of the imaging elements at a predetermined imaging timing and stores each detected light intensity value indicated by the light intensity signal as two-dimensional image data in an image storage area set in a memory, and an image processing section that produces data for inspection by processing the two dimensional image data, and the imaging device images an object while the object is moved relative to the imaging device in the X-axis direction.

Then the imaging control section adjusts the imaging timing so as to synchronize a projected image unit moving time, which is a time for the projected image of the object to move by "m" pixels ("m" is an integer number greater than or equal to 1) in the X-axis direction on the imaging elements, with an imaging time interval, which is a time interval to receive the light intensity signal from the imaging elements and to store it as a single unit of two-dimensional image data in accordance with the object in the image storage area, and the image processing section comprises a specifying section that specifies partial image data imaged at the identical inspection position on the object respectively from the two-dimensional image data based on the object appearing deviated by "m" pixels in the X-axis direction in each unit of the two-dimensional image data imaged at each of the imaging timings, and a data producing section that produces data for inspection in which a noise reducing process is provided at the inspection position based on each section of the partial image data.

As an inspection system wherein an effect of this invention is especially remarkable, the inspection system may further comprise a grid pattern forming device that forms a grid pattern wherein grid units comprising a bright section and a dark section having a constant width are continuously arranged, and the grid pattern is arranged at a focal position of the imaging device and the object is arranged on an optical path between the grid pattern and the imaging device respectively, "n" ("n" is an integer number greater than or equal to 1) pieces of the grid unit are so arranged to correspond to $Xn±α$ ($X=4p$ (p is an integer number greater than or equal to 1), $α<<n$) pieces of the imaging elements in the projected image of the grid pattern on the imaging elements, and the data producing section comprises an optical distortion calculating section that calculates an optical distortion amount generated at each section of the partial image data at the inspection position from Moire fringes appearing on the partial image data due to the grid pattern, and a noise reducing section that integrates the optical distortion amount in accordance with each section of the partial image data and produces the data for inspection.

As a concrete arrangement of the optical distortion calculating section, the optical distortion calculating section may comprise a sine wave producing section that extracts and produces multiple kinds of sine waves whose phases are displaced by 90° respectively from the image data of the Moire fringes, a phase angle calculating section that calculates a phase angle of the Moire fringes at each of the imaging elements from each of the sine waves, and a distortion amount calculating section that calculates the optical distortion amount from a difference of the phase angles between each of the imaging elements.

This invention can be applied to not only the inspection system but also an imaging device having less noise.

The imaging device may comprise multiple imaging elements arranged in two-dimensions along an X-axis and a Y-axis which are two virtual orthogonal axes, an imaging control section that receives a light intensity signal from all or a part of the imaging elements at a predetermined imaging timing and stores each light intensity value indicated by the light intensity signal in an image storage area set in a memory as two-dimensional image data, and an image processing section that produces noise-reduced data by processing the two-dimensional image data, wherein an object is imaged while the object is moved relative to the imaging device in the X-axis direction, and characterized in that the imaging control section adjusts the imaging timing so as to synchronize a projected image unit moving time, which is a time for the projected image of the object to move by "m" pixels ("m" is an integer number greater than or equal to 1) in the X-axis direction on the imaging elements, with an imaging time interval, which is a time interval to receive the light intensity signal from the imaging elements and to store it as a single unit of two-dimensional image data in accordance with the object in the image storage area, and the image processing section comprises a specifying section that specifies partial image data imaged at the identical position on the object respectively from each unit of the two-dimensional image data based on the object appearing deviated by "m" pixels in the X-axis direction in each unit of the two-dimensional image data imaged at each of the imaging timings, and a data producing section that produces noise-reduced data in which a noise reducing process is provided at the position based on each section of the partial image data.

In addition, the present claimed invention is also applied to an inspection method.

More specifically, the inspection method may be an inspection method that images and inspects the object by the use of an imaging device while the object is moved in an X-axis direction relative to the imaging device, the imaging device having multiple imaging elements arranged in two-dimensions along the X-axis and a Y-axis, which are two virtual orthogonal axes, and an imaging control section that receives a light intensity signal from all or a part of the imaging elements at a predetermined imaging timing and stores each light intensity value indicated by the light intensity signal in an image storage area set in a memory as two-dimensional image data, and characterized by comprising a synchronizing step that adjusts the imaging timing so as to synchronize a projected image unit moving time, which is a time for the projected image of the object to move by "m" pixels ("m" is an integer number greater than or equal to 1) in the X-axis direction on the imaging elements, with an imaging time interval, which is a time interval to receive the light intensity signal from the imaging elements and to store it as a single unit of two-dimensional image data in accordance with the object in the image storage area, a specifying step that specifies partial image data imaged at the identical inspection position on the object in the multiple units of two-dimensional image data imaged at each of the imaging timings based on the object appearing deviated by "m" pixels in the X-axis direction in each of the units of two-dimensional image data due to a difference of the imaging time, and a data producing step that produces data for inspection in which a noise reducing process is provided at the inspection position based on each section of the partial image data.

In this case, it is more preferable if a grid pattern, wherein grid units comprising a bright section and a dark section having a constant width are continuously arranged, is arranged at a focal position of the imaging device and the object is arranged on an optical path between the grid pattern and the imaging device respectively, and "n" ("n" is an integer number greater than or equal to 1) pieces of the grid unit are so arranged to correspond to $Xn \pm \alpha$ ($X=4p$ ($p$ is an integer number greater than or equal to 1), $\alpha << n$) pieces of the imaging elements in the projected image of the grid pattern on the imaging elements, and an optical distortion calculating step is performed that calculates an optical distortion amount generated at each section of the partial image data from Moire fringes appearing on the partial image data due to the grid pattern, and a noise reducing step is performed that integrates the optical distortion amount in accordance with each section of the partial image data and produces the data for inspection, in the data producing step.

Effect of the Invention

In accordance with this invention, since the detected light intensity value from each of the imaging elements is stored once in the image storage area every time the image is taken and a calculation is conducted on the data stored in the image storage area, merits can be enjoyed such that there is a lot of flexibility in an arithmetic processing so that various processing can be conducted easily compared with a case that data for every imaging is automatically integrated like the TDI. In addition, since an inexpensive area image sensor such as a CMOS sensor can be used as the imaging element, a cost can be reduced.

Furthermore, since each optical distortion amount calculated at the identical position of the object is measured at portions where the grid pattern is different, it is possible to reduce a cause of the noise such as the fluctuation of the width of the bright section and the dark section of the grid pattern, the fluctuation of the width (the pitch width) of the grid units, or dust on the grid pattern, and only the optical distortion of the glass board can be emphasized by integrating the amount of the optical distortion. Then an S/N ratio is improved so that a measurement can be conducted accurately.

EXPLANATION OF REFERENCE CHARACTERS

100 . . . inspection system
1 . . . grid pattern forming device
11 . . . grid pattern
1a . . . grid unit
2 . . . imaging device
22 . . . imaging element (CMOS sensor)
232 . . . memory
3 . . . imaging control section
4 . . . image processing section
41 . . . specifying section
42 . . . data producing section
421 . . . optical distortion calculating section
422 . . . noise reducing section
421a . . . sine wave producing section
421b . . . phase angle calculating section
421c . . . distortion amount calculating section
D1 . . . image storage area

BEST MODES OF EMBODYING THE INVENTION

One embodiment of the present claimed invention will be explained with reference to drawings.

Figure 1:
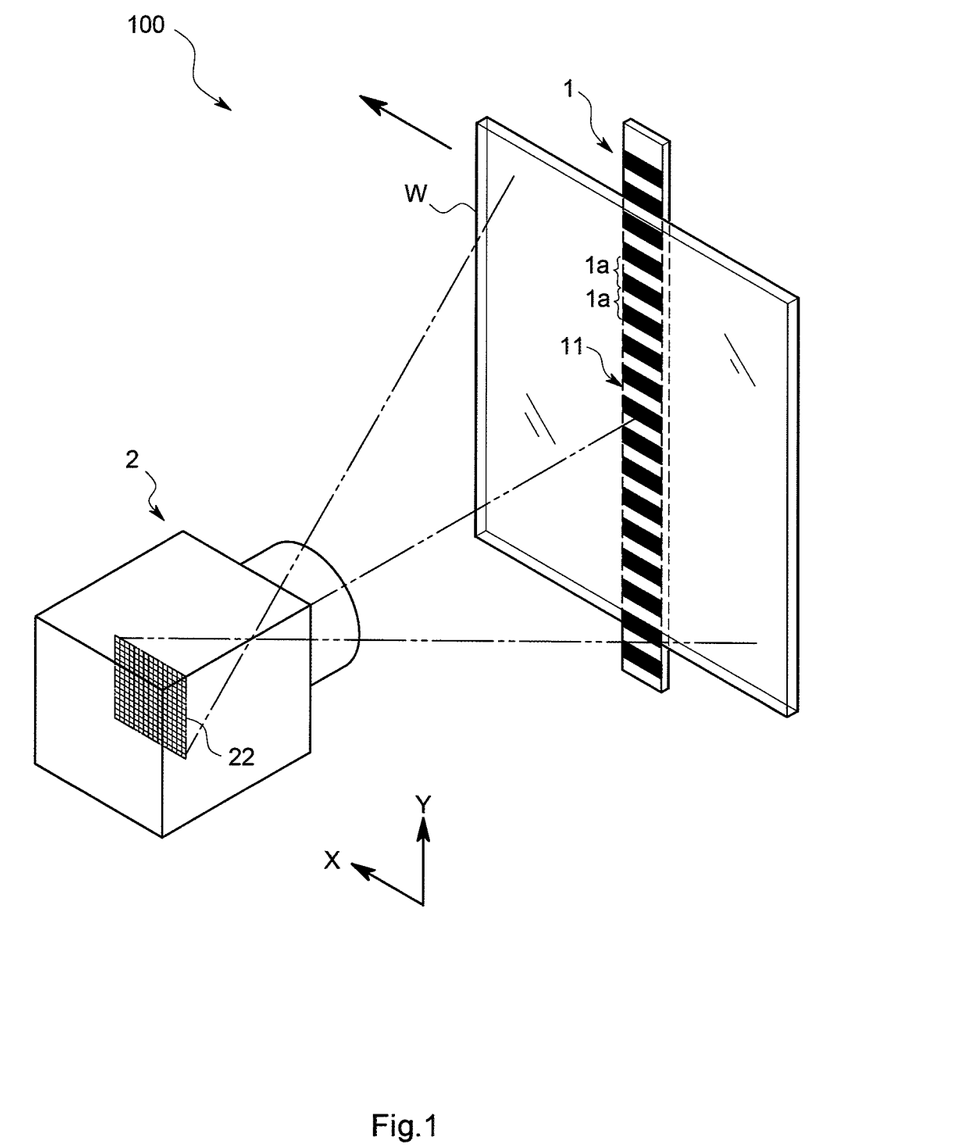
FIG. 1 is an overall pattern diagram of an inspection system in accordance with one embodiment of the present claimed invention.

An inspection system 100 in accordance with this invention comprises, as shown in FIG. 1, a grid pattern forming device 1 and an imaging device 2 and is so arranged to move a transparent glass board W, which is an object to be inspected, in one direction between the grid pattern forming device 1 and the imaging device 2 by means of a transporting device, not shown in drawings, for scanning and imaging.

Figure 2:
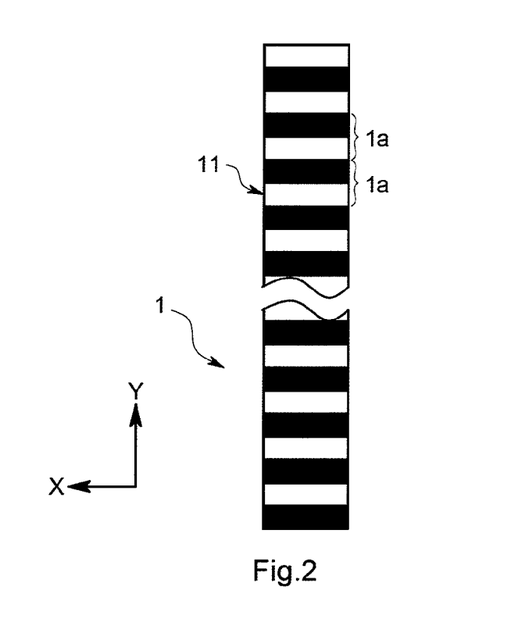
FIG. 2 is a front view of a grid forming device in accordance with this embodiment.

As shown in FIG. 1 and FIG. 2, the grid pattern forming device 1 forms a grid pattern 11 comprising continuous multiple grid units 1a each of which comprises a bright section and a dark section having a constant width. In this embodiment, the grid pattern 11 is depicted on a long rectangular plate. In addition, for example, the long rectangular plate may be backlit from behind or a grid pattern may be formed by arranging a light source such as an LED or a fluorescent light and a shielding member alternately. The grid pattern forming device 1 is arranged on a back surface of the glass board W with a direction of repeating the bright section and the dark section orthogonal to a direction of moving the glass board W.

The transporting device, not shown in drawings, utilizes a roller that moves the glass board W at a constant speed, for example, by pinching side edge sections of the glass board W from a direction of its thickness. In addition to this, the transporting device may be, for example, an X-Y stage.

Figure 5:
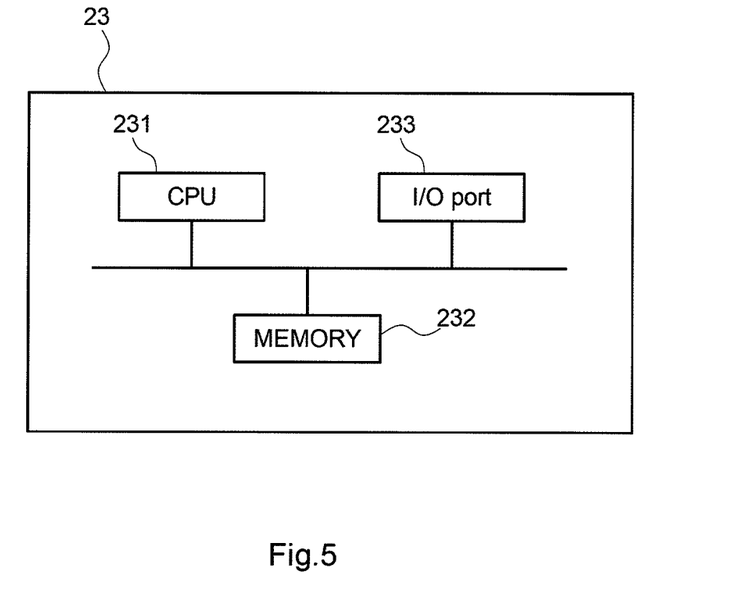
FIG. 5 is a physical structure view of an information processing unit in accordance with this embodiment.
Figure 6:
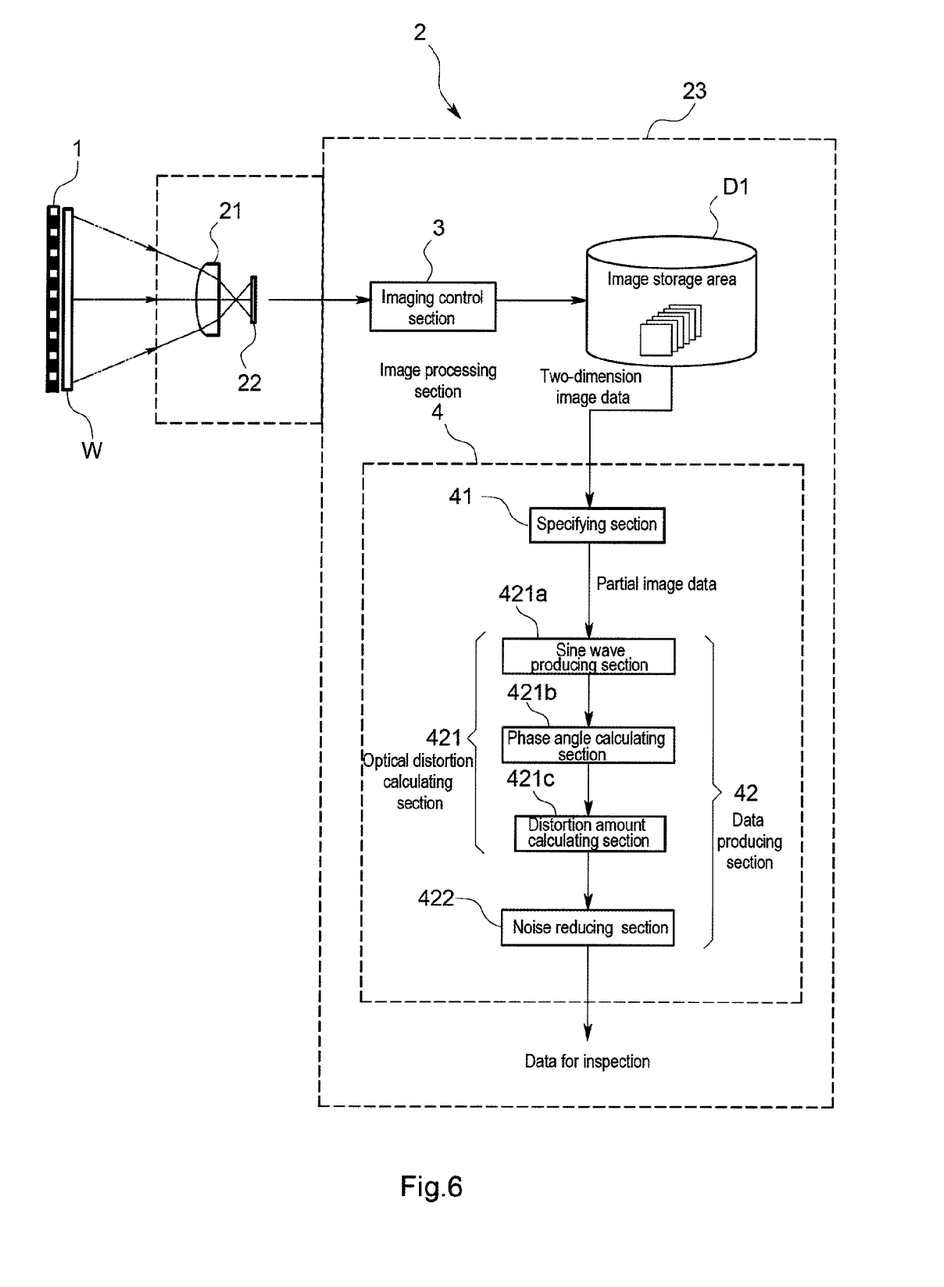
FIG. 6 is a functionally internal structure view of an imaging device in accordance with this embodiment.

The imaging device 2 comprises, as shown in FIG. 1 FIG. 5, and FIG. 6, an optical member 21, multiple imaging elements 22 arranged at a back side of the optical member 21 and an information processing device 23 that receives and processes a light intensity signal from each of the imaging elements 22, each of which is housed in a body. An imaging surface of the imaging device 2 is arranged to face a surface (a surface to be inspected) of the glass board W.

If the imaging device 2 is described in detail, the optical member 21 comprises a combination of lenses and its focal point is adjusted to the grid pattern 11.

In this embodiment, the imaging element 22 uses, for example, a CMOS sensor. The reason is that the CMOS sensor is relatively inexpensive and an amplifier is integrally incorporated into each photodiode (not shown in drawings) as being a light sensitive element so that it is easy to read out the light intensity signal. A CCD or other imaging element may be used as the imaging element 22.

Figure 3:
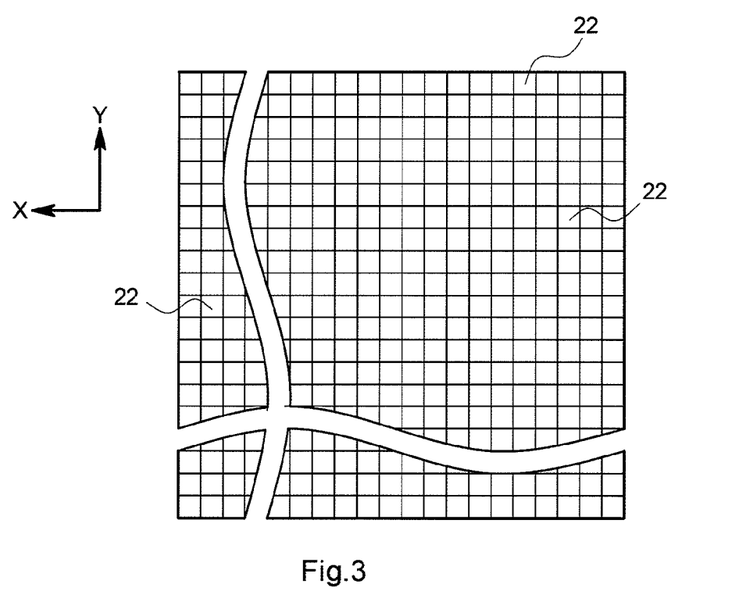
FIG. 3 is a front view of an imaging element group in accordance with this embodiment.
Figure 4:
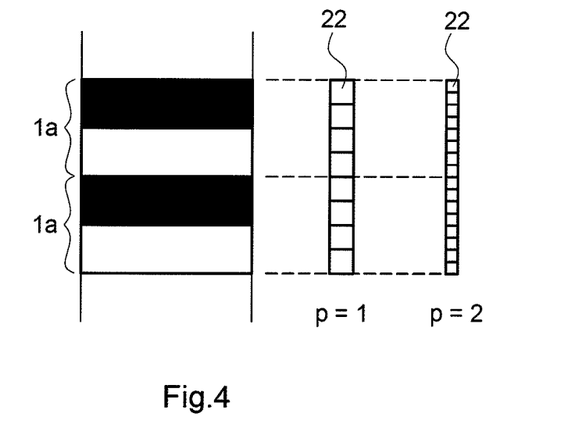
FIG. 4 is a relation explanatory view showing a relationship between a grid unit width and a number of an imaging element in accordance with this embodiment.

An imaging element group in a rectangular plate shape is formed, as shown in FIG. 1 and FIG. 3, by arranging the imaging elements 22 two-dimensionally along an X-axis and a Y-axis, which are two virtual orthogonal axes. In this embodiment, a posture of the imaging device 2 is so set that a direction of the X-axis coincides with a moving direction of the glass board W and the X-Y plane is parallel to the surface of the glass board W. In addition, a distance between the imaging device 2 and the grid pattern 11 or an imaging magnification is so set that "n" ("n" is an integer number greater than or equal to 1) pieces of the grid unit 1a correspond to $Xn \pm \alpha$ ($X=4p$ (p is an integer number greater than or equal to 1), $\alpha<<n$) pieces of the imaging elements 22 in the projected image of the grid pattern 11 on the imaging element 22. With this arrangement, Moire fringes determined by a value of $\alpha$, which is a deviance, appear on the two-dimensional image data. To help understanding, a relationship between the imaging elements 22 and the grid pattern 11 is shown in FIG. 4. As mentioned, the imaging device 2 comprises a two-dimensional area sensor (a group of imaging elements 22 arranged two-dimensionally), however, the imaging elements 22 arranged in a line along the Y-axis direction of the two-dimensional area sensor are used for this inspection system 100 as a function of the line sensor (detail will be described later).

The information processing device 23 physically comprises, as shown in FIG. 5, a CPU 231, a memory 232 and an I/O port 233 for communication, and is incorporated into the body of the imaging device 2. As shown in FIG. 6, the information processing device 23 produces the functions of an imaging control section 3 and an image processing section 4 by cooperatively working the CPU 231 or its peripheral devices based on a program set in a predetermined area of the memory 232. All of the functions of the information processing device 23 are not necessarily incorporated into the body. For example, a part of the functions (especially the image processing section 4) may be produced by other computers by making the information processing device 23 communicable with other computers. Next, each of the above-mentioned function sections will be explained.

The imaging control section 3 receives the light intensity signal from each of the imaging elements 22 at a predetermined imaging timing and stores each value of the light intensity shown by the light intensity signal as the two-dimensional image data in an image storage area D1 set in the memory 232. In this embodiment, the imaging timing is adjusted so that a unit moving time of the projected image of the glass board W, which is a time for the projected image to move by one pixel in the X-axis direction on the imaging element 22, is synchronized with an imaging time interval, which is a time interval when the light intensity signal is received from the imaging element 22 and stored in the image storage area D1 as a single unit of two-dimensional image data in accordance with the object.

The image processing section 4 produces data for inspection by processing the two-dimensional image data in the image storage area D1. More concretely, as shown in FIG. 6, the image processing section 4 comprises a specifying section 41 that specifies each section of the partial image data imaged at the identical inspection position on the glass board W from each unit of the two-dimensional image data, respectively, based on an image of the glass board W appearing deviated by one pixel in the X-axis direction in each unit of the two-dimensional data imaged at each of the imaging timings, namely, stored in the image storage area D1, and a data producing section 42 that produces data for inspection in which a noise reducing process is provided at the inspection position based on each section of the partial image data.

In addition, the data producing section 42 comprises an optical distortion calculating section 421 that calculates an amount of the optical distortion generated at each section of the partial image data at the inspection position based on the Moire fringes (shown in FIG. 8) appearing on the partial image data due to the grid pattern 11 and a noise reducing section 422 that integrates and averages the amount of the optical distortion in accordance with each section of the partial image data and produces the data for inspection.

Furthermore, if the optical distortion calculating section 421 is described in more detail, the optical distortion calculating section 421 comprises a sine wave producing section 421a that extracts and produces several different kinds of the sine waves whose phases deviate by 90° respectively from the image data of the Moire fringes, a phase angle calculating section 421b that calculates a phase angle of the Moire fringes in each of the imaging elements 22 from each of the sine waves, and a distortion amount calculating section 421c that calculates the amount of the optical distortion from a difference of the phase angles between the imaging elements 22.

Next, the inspection system 100 having the above arrangement will be explained by focusing on an operation of the imaging device 2 with reference to FIGS. 7(a)-7(c).

When the glass board W is transported, the imaging device 2 obtains two-dimensional image data imaged in a certain area of the grid pattern 11 and the glass board W passes over the grid pattern 11 one after another at the imaging timing synchronized with the moving speed of the glass board W and transfers the two-dimensional image data to the image storage area D1 and stores it. A number of the stored two-dimensional image data is a number of pieces of the imaging elements 22 of the grid pattern image appearing on the imaging elements 22 in a width along the X-axis. In this embodiment, the number of the imaging elements 22 is set as "M" pieces.

Next, in the first two-dimensional image data, an image processing is conducted on the partial image data obtained from one predetermined line along the Y-axis of the imaging elements 22, namely a detected light intensity value of each of the imaging elements 22.

Figure 7:
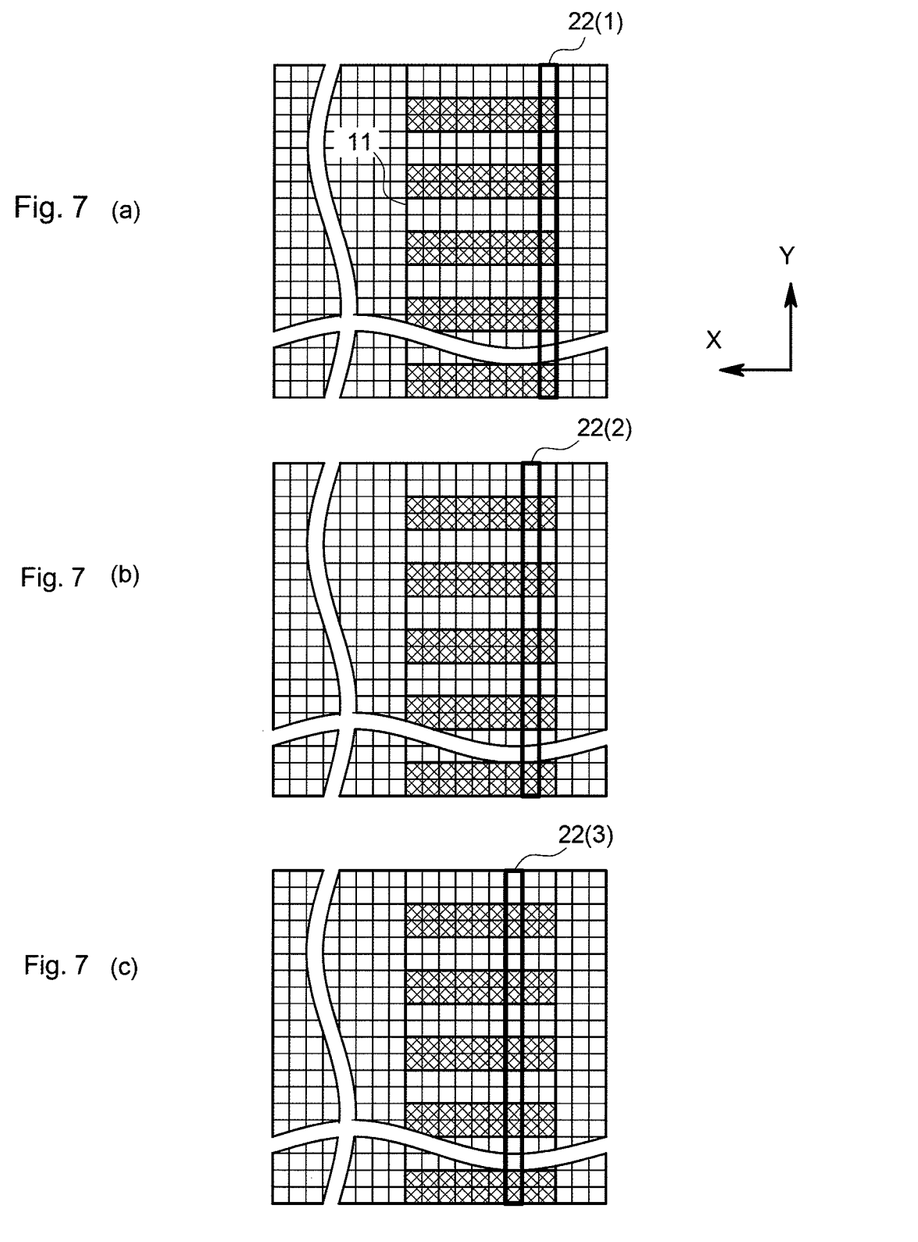
FIGS. 7(a), 7(b), and 7(c) are explanatory views of an inspection position specifying method in order to explain a method for specifying an inspection position in this embodiment.
Figure 8:
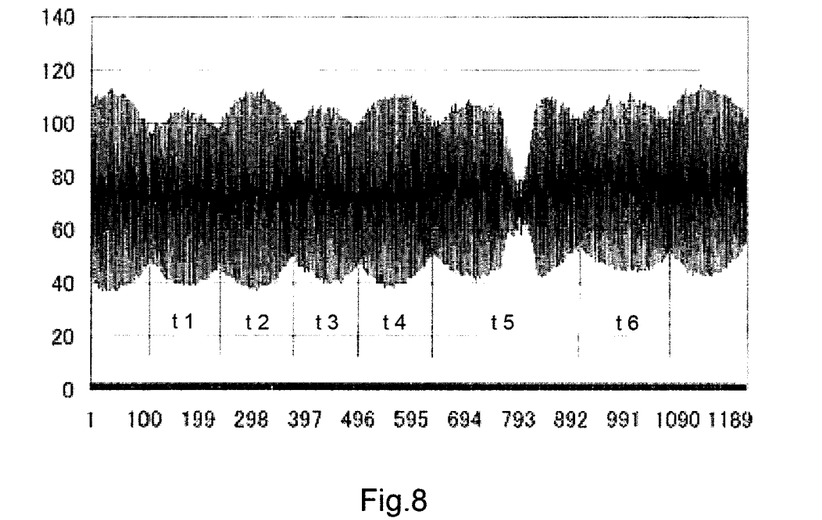
FIG. 8 is a graph showing image data and Moire fringes in this embodiment.

If explained more concretely, one predetermined line of the imaging elements 22 is, as shown by a black border in FIG. 7(a), one line located at the most end part of the grid pattern image of the imaging elements 22. In order to classify the imaging elements 22, this line of the imaging elements is hereinafter denoted as 22(1). A graph (namely, the partial image data) made for this line of the imaging elements 22(1) with a number of the imaging elements plotted on the X-axis and the detected value of the light intensity from each of the imaging elements plotted on the Y-axis shows a zonal line due to the grid pattern 11, and the width of the zonal line fluctuates in a constant cycle and then the Moire fringes appear as shown in FIG. 8.

Figure 9:
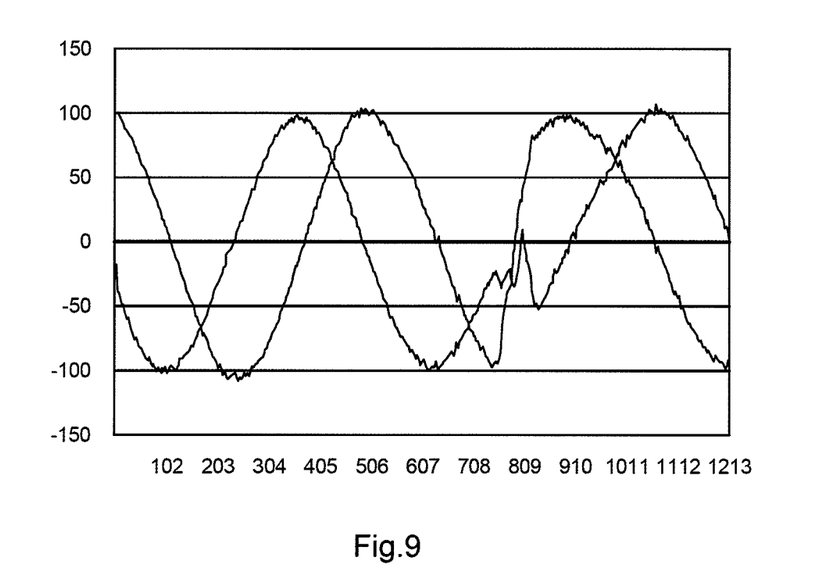
FIG. 9 is a graph showing a sine wave extracted from the Moire fringes in this embodiment.

Next, several different kinds of the sine waves having phases deviated by 90° respectively are extracted from the Moire fringes (refer to FIG. 9). Then a phase angle of the Moire fringes appearing on the detected light intensity value of each of the imaging elements 22 is calculated from each of the sine waves (refer to FIG. 10). The amount of the optical distortion is calculated from a difference of the phase angles between the imaging elements 22.

The principle that the amount of the optical distortion can be calculated from the difference of the phase angles between the imaging elements 22 will now be conceptually explained (refer to the patent document 1 for more detail).

Figure 10:
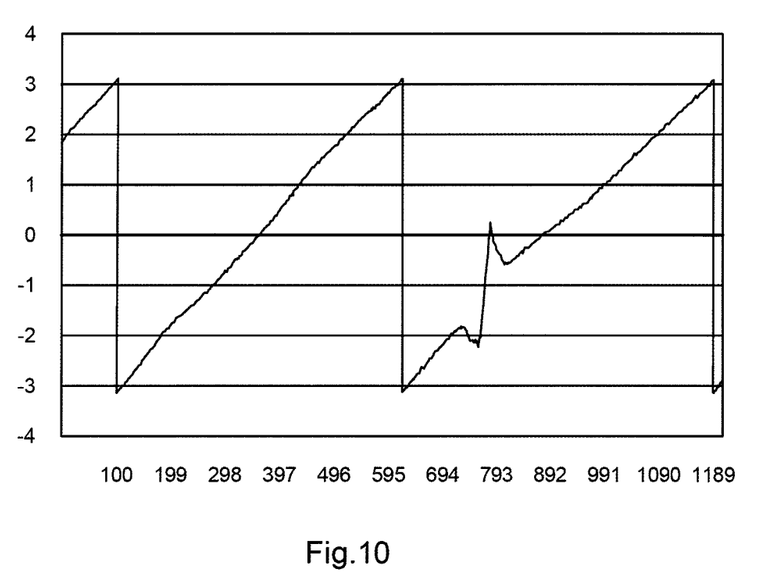
FIG. 10 is a graph showing a phase angle of each imaging element calculated from the sine wave in this embodiment.

On the condition that there is no defect on the glass board W so that no optical distortion is generated, the Moire fringes will form a most perfect sine wave and the phase angle of the detected light intensity value of each of the imaging elements 22 will increase constantly according to the most perfect sine wave. Practically the phase angle will increase from 0° to 359° and return to 0°. Then the graph of the ideal phase angle of each of the imaging elements 22 shows a triangle wave as shown in FIG. 10. If a calculation is conducted by considering a change of the phase angle from 359° to 0° and a difference between the adjacent imaging elements 22 is plotted on the Y-axis and an order of each of the imaging elements 22 is plotted on the X-axis, the graph shows a horizontal straight line.

Figure 11:
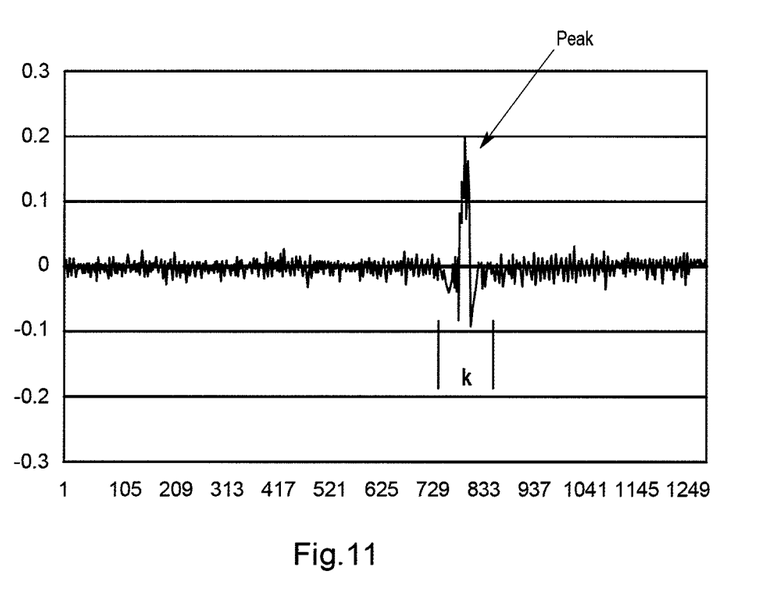
FIG. 11 is a graph showing an amount of the optical distortion calculated after the phase angle is calculated in this embodiment.

Meanwhile, if an optical distortion is generated due to a defect of the glass board W, the Moire fringes are disturbed and the disturbance makes a peak as shown in FIG. 11 on the graph of the horizontal straight line. The amount of the optical distortion can be calculated from an amount of the peak.

However, practically noise is generated due to white noise of the imaging elements 22, fluctuation of a width of the bright section and the dark section of the grid pattern 11, fluctuation of a width (a pitch width) of the grid units 1a, or dust on the grid pattern 11. As shown in a graph of FIG. 11, the noise appears as fine waves. Then since a subtle surge or an irregularity on the surface of the glass board W can appear as a peak having a smaller height than that of the fine waves, there might be a case of failing to detect the subtle surge or the irregularity on the surface of the glass board W because it is buried in the noise.

In this embodiment, since the image of the glass board W in the two-dimensional image data obtained in the next imaging timing appears deviated by one pixel in the X-axis direction from the image of the first two-dimensional image data (refer to FIG. 7(b)), a line of the imaging element 22(2) that is next to the first one line of the imaging element 22(1) used for calculating the optical distortion is specified as the partial image data imaged at the identical position of the glass board W, and the amount of the optical distortion is calculated from the partial image data obtained from the imaging element 22(2), namely, the detected light intensity value of each of the imaging elements 22 by means of the same procedure as that of the above-mentioned. Next, the amount of the optical distortion is calculated based on the detected light intensity value from the imaging element 22(3) in the third two-dimensional image data.

Since the grid pattern 11 has a width of multiple pixels (for example, "M" pixels) in the X-axis direction, the amount of the optical distortion is calculated by conducting the same procedure on the two-dimensional image data imaged continuously at "M" times.

Next, the data in accordance with the final amount of the optical distortion wherein a noise is reduced, namely the data for inspection is produced by integrating and averaging "M" pieces of the calculated amounts of the optical distortion.

Since each amount of the optical distortion calculated from the identical position of the glass board W is measured at a position where the grid pattern 11 differs respectively, it is possible to reduce a cause of the noise such as the fluctuation of the width of the bright section and the dark section of the grid pattern 11, the fluctuation of the width (the pitch width) of the grid unit 1a or the dust on the grid pattern 11, and only the optical distortion of the glass board W can be emphasized by integrating each of the amounts of the optical distortion. Then an S/N ratio is improved so that a measurement can be conducted accurately.

In addition, in accordance with this embodiment, since the detected light intensity value from each of the imaging elements 22 is stored once in the image storage area D1 every time the image is taken and a calculation is conducted on the data stored in the image storage area D1, there is a lot of flexibility in the arithmetic processing so that various processing can be conducted easily compared with a case that data for every imaging is automatically integrated like the above-mentioned TDI.

Figure 12:
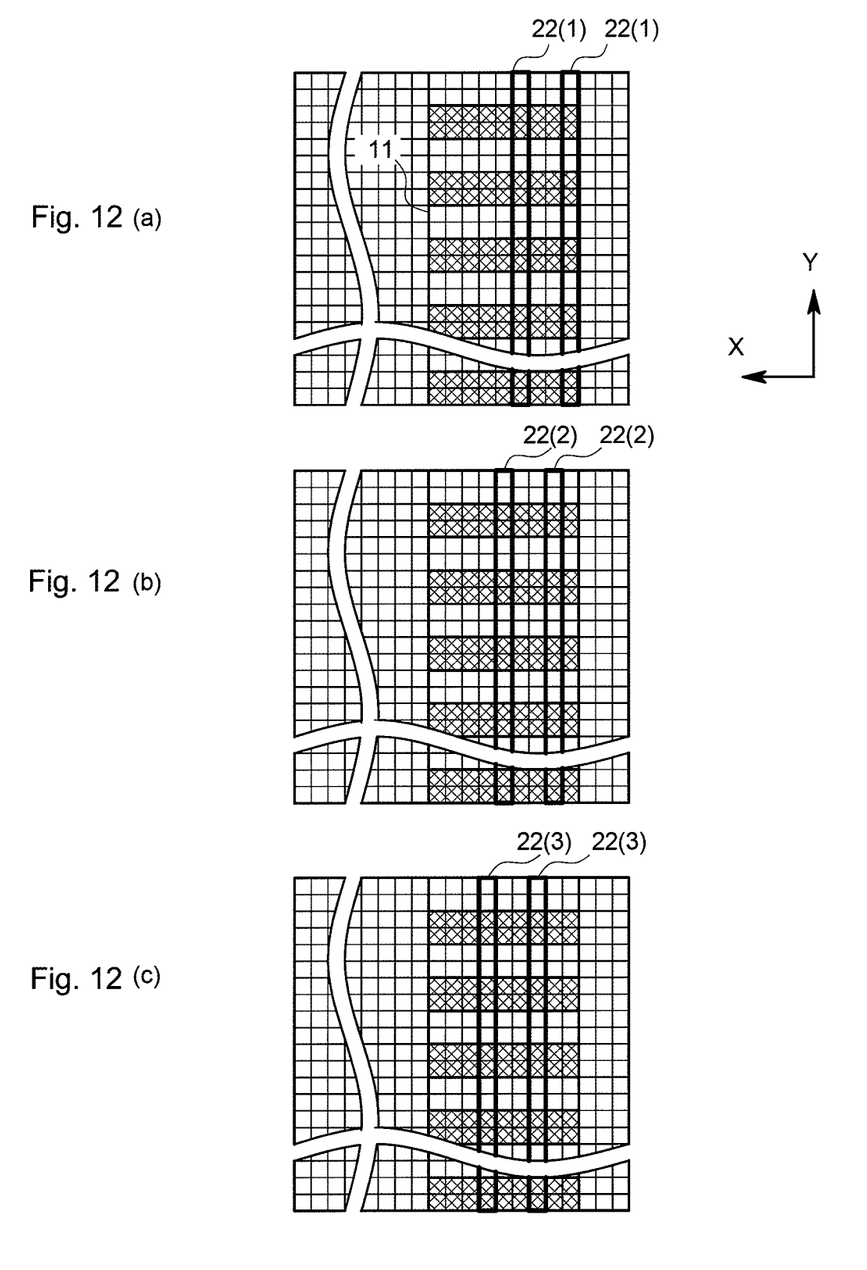
FIGS. 12(a), 12(b), and 12(c) are explanatory views of an inspection position specifying method in order to explain a method for specifying an inspection position in another embodiment of this invention.

The present claimed invention is not limited to the above-mentioned embodiment. For example, the amount of the optical distortion is calculated by focusing on only one line of the imaging element 22 in the above-mentioned embodiment, however, it is also possible to calculate the amount of the optical distortion across a broader range by conducting parallel processing on multiple lines (for example, two lines) of the imaging elements 22 as shown in FIGS. 12(a)-12(c). The multiple lines may be separated or continuous.

Figure 13:
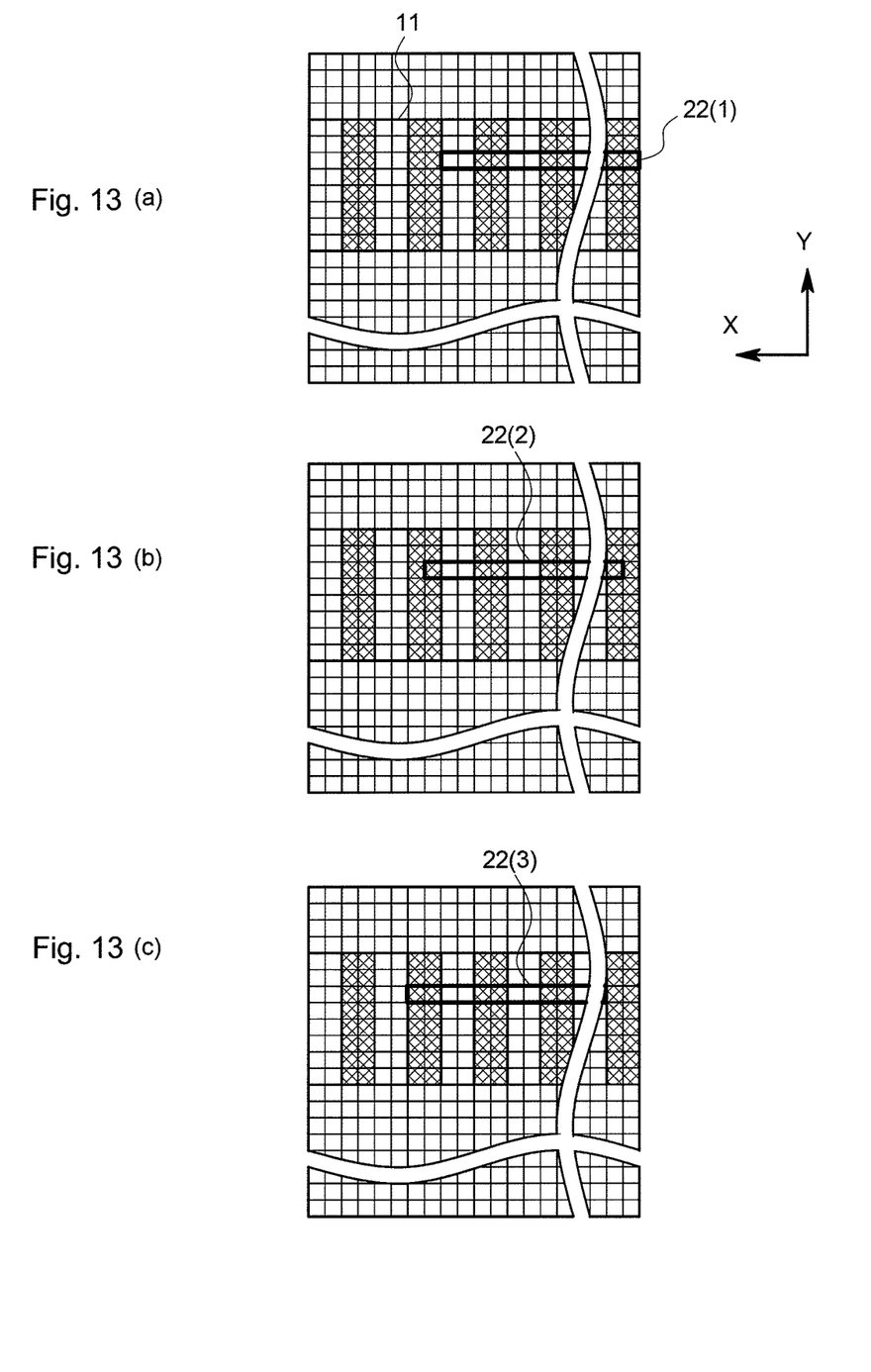
FIGS. 13(a), 13(b), and 13(c) are explanatory views of a method for specifying an inspection position in order to explain a method for specifying an inspection position in a further different embodiment of this invention.

In addition, the grid pattern 11 may be arranged so as to have the direction of repeating the bright section and the dark section in the grid pattern 11 coincide with a relative moving direction of the glass board W as shown in FIGS. 13(a)-13(c). In this case, as shown in a black border in FIGS. 13(a)-13(c), the amount of the optical distortion is calculated by using a part or all of one line of the imaging elements 22 along the X-direction by means of the same procedure as that of the above-mentioned. A length of the grid pattern 11 in the X-direction on the imaging element 22 has to be longer than a number of one line of the imaging elements 22 used in the above-mentioned calculation of the optical distortion.

Furthermore, in the above-mentioned embodiment, the light intensity signal from all of the imaging elements is transferred to and stored in the image storage area as the two-dimensional image data at every imaging timing, however, only partial image data may be transferred to and stored in the image storage area. In this case, only partial image data imaged at the identical position of an object (taking the first embodiment as an example, only data from one line of the imaging elements 22 is deviated by one line) may be transferred to the storage area and then the amount of the optical distortion is calculated by conducting an image processing on the partial image data. With this arrangement, since an amount of the data to be transferred to the image storage area can be reduced, it is possible to shorten an interval of the imaging timing so as to speed up the time required for imaging.

Figure 14:
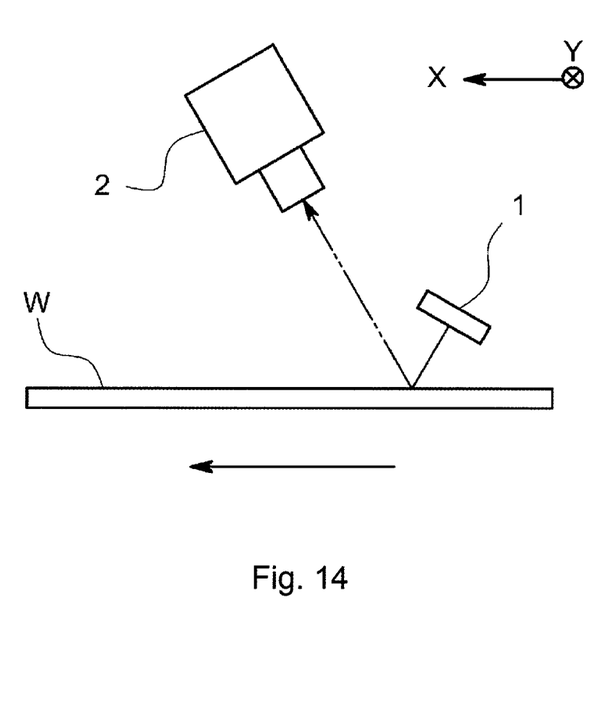
FIG. 14 is an overall pattern diagram of an inspection system in accordance with a further different embodiment of the present claimed invention.

In addition, the object to be inspected is the transparent board in the above-mentioned embodiment, however, this invention may be applied also to an opaque object with a mirror finish. In this case, as shown in FIG. 14, the imaging device 2 and the grid forming device may be arranged at the same side as the object to be inspected so that the light from the grid pattern 11 reflects on a surface to be inspected of the object and is taken into the imaging device 2.

Furthermore, the imaging device in accordance with this invention is not limited to the use for inspection. More specifically, image data with reduced noise (noise-reduced data) may be output without calculating the amount of the optical distortion from each of the partial image data.

The present claimed invention is not limited to the above-mentioned embodiment and it is a matter of course that this invention may be variously modified without departing from the spirit of the invention.

POSSIBLE APPLICATIONS IN INDUSTRY

In accordance with this invention, since the detected light intensity value from each of the imaging elements is stored once in the image storage area every time the image is taken and a calculation is conducted on the data stored in the image storage area, there is a lot of flexibility in the arithmetic processing so that various processing can be conducted easily compared with a case that data for every imaging is automatically integrated like the TDI.

The invention claimed is:

1. An inspection system comprising an imaging device having multiple imaging elements arranged in two-dimensions along an X-axis and a Y-axis which are two virtual orthogonal axes, an imaging control section that receives a light intensity signal from all or a part of the imaging elements at a predetermined imaging timing and stores each detected light intensity value indicated by the light intensity signal as two-dimensional image data in an image storage area (D1) set in a memory, and an image processing section that produces data for inspection by processing the two-dimensional image data, wherein an object (W) for inspection is imaged by the imaging device while the object is moved relative to the imaging device in an X-axis direction that is substantially parallel to the X-axis of the imaging elements, and characterized in that the imaging control section adjusts the imaging timing so as to synchronize in time a projected image unit moving time with an imaging time interval, wherein the projected image unit moving time is a time for the projected image of the object to move by "m" pixels as the object is moved in the X-axis direction relative to the imaging device, wherein "m" is an integer number greater than or equal to 1, in the X-axis direction on the imaging elements, and wherein the imaging time interval is a time interval to receive the light intensity signal from the imaging elements and to store it as a single unit of two-dimensional image data in accordance with the object (W) in the image storage area (D1), and the image processing section comprises
a specifying section that specifies partial image data imaged at an identical inspection position on the object (W) respectively from each unit of the two-dimensional image data based on the object (W) appearing deviated by "m" pixels in the X-axis direction in each unit of the two-dimensional image data imaged at each of the imaging timing, and
a data producing section that produces data for inspection in which an optical distortion calculation and a noise reduction are executed at the inspection position based on each section of the partial image data; and
wherein the inspection system further comprises: a grid pattern forming device that forms a grid pattern wherein grid units comprising a bright section and a dark section having a constant width are continuously arranged, and the grid pattern is arranged at a focal position of the imaging device and the object (W) is arranged on an optical path between the grid pattern and the imaging device respectively, and "n", wherein "n" is an integer number greater than or equal to 1, pieces of the grid units are so arranged to correspond to $Xn\pm\alpha$, wherein $X=4p$, p is an integer number greater than or equal to 1, and $\alpha<<n$, pieces of the imaging elements in the projected image of the grid pattern on the imaging elements, wherein the data producing section comprises an optical distortion calculating section that calculates an optical distortion amount generated at each section of the partial image data at the inspection position from Moire fringes appearing on the partial image data due to the grid pattern, and a noise reducing section that integrates the optical distortion amount in accordance with each section of the partial image data and produces data for inspection.

2. The inspection system described in claim 1, wherein the optical distortion calculating section comprises
   a sine wave producing section that extracts and produces multiple kinds of sine waves whose phases are displaced by 90° respectively from image data of the Moire fringes,
   a phase angle calculating section that calculates a phase angle of the Moire fringes at each of the imaging elements from each of the sine waves, and
   a distortion amount calculating section that calculates the optical distortion amount from a difference of the phase angles between each of the imaging elements.

3. An imaging device comprising multiple imaging elements arranged in two-dimensions along an X-axis and a Y-axis which are two virtual orthogonal axes, an imaging control section that receives a light intensity signal from all or a part of the imaging elements at a predetermined imaging timing and stores each light intensity value indicated by the light intensity signal in an image storage area (D1) set in a memory as two-dimensional image data, and an image processing section that produces noise-reduced data by processing the two-dimensional image data, wherein an object (W) for inspection is imaged while the object (W) is moved relative to the imaging device in an X-axis direction that is substantially parallel to the X-axis of the imaging elements, and characterized in that
   the imaging control section adjusts the imaging timing so as to synchronize in time a projected image unit moving time with an imaging time interval, wherein the projected image unit moving time is a time for the projected image of the object (W) to move by "m" pixels as the object is moved in the X-axis direction relative to the imaging device, wherein "m" is an integer number greater than or equal to 1, in the X-axis direction on the imaging elements, and wherein the imaging time interval is a time interval to receive the light intensity signal from the imaging elements and to store it as a single unit of two-dimensional image data in accordance with the object (W) in the image storage area (D1), and
   the image processing section comprises
      a specifying section that specifies partial image data imaged at an identical inspection position on the object (W) respectively from each unit of the two-dimensional image data based on the object (W) appearing deviated by "m" pixels in the X-axis direction in each unit of the two-dimensional image data imaged at each of the imaging timings, and
      a data producing section that produces noise-reduced data in which an optical distortion calculation and a noise reduction are executed at the inspection position based on each section of the partial image data; and wherein the inspection system further comprises: a grid pattern forming device that forms a grid pattern wherein grid units comprising a bright section and a dark section having a constant width are continuously arranged, and the grid pattern is arranged at a focal position of the imaging device and the object (W) is arranged on an optical path between the grid pattern and the imaging device respectively, and "n", wherein "n" is an integer number greater than or equal to 1, pieces of the grid units are so arranged to correspond to $Xn\pm\alpha$, wherein $X=4p$, p is an integer number greater than or equal to 1, and $\alpha<<n$, pieces of the imaging elements in the projected image of the grid pattern on the imaging elements, wherein the data producing section comprises an optical distortion calculating section that calculates an optical distortion amount generated at each section of the partial image data at the inspection position from Moire fringes appearing on the partial image data due to the grid pattern, and a noise reducing section that integrates the optical distortion amount in accordance with each section of the partial image data and produces data for inspection.

4. An inspection method that images and inspects an object (W) for inspection using an imaging device while the object (W) is moved relative to multiple imaging elements of the imaging device in an X-axis direction that is substantially parallel to an X-axis of the imaging elements, the multiple imaging elements being arranged in two-dimensions along the X-axis and a Y-axis which are two virtual orthogonal axes, and an imaging control section that receives a light intensity signal from all or a part of the imaging elements at a predetermined imaging timing and stores each light intensity value indicated by the light intensity signal in an image storage area (D1) set in a memory as two-dimensional image data, and characterized by comprising
   a synchronizing step that adjusts the imaging timing so as to synchronize in time a projected image unit moving time with an imaging time interval, wherein the projected image unit moving time is a time for the projected image of the object (W) to move by "m" pixels as the object is moved in the X-axis direction relative to the imaging device, wherein "m" is an integer number greater than or equal to 1, in the X-axis direction on the imaging elements, and wherein the imaging time interval is a time interval to receive the light intensity signal from the imaging elements and to store it as a single unit of two-dimensional image data in accordance with the object (W) in the image storage area (D1),
   a specifying step that specifies partial image data imaged at an identical inspection position on the object (W) from each of the multiple units of two-dimensional image data imaged at each of the imaging timings based on the object (W) appearing deviated by "m" pixels in the X-axis direction in each unit of the two-dimensional image data due to a difference of the imaging time, and
   a data producing step that produces data for inspection in which an optical distortion calculation and a noise reduction are executed at the inspection position based on each section of the partial image data; wherein the inspection system further comprises: a grid pattern forming device that forms a grid pattern wherein grid units comprising a bright section and a dark section having a constant width are continuously arranged, and the grid pattern is arranged at a focal position of the imaging device and the object (W) is arranged on an optical path between the grid pattern and the imaging device respectively, and "n", wherein "n" is an integer number greater than or equal to 1, pieces of the grid units are so arranged to correspond to $Xn \pm \alpha$, wherein $X=4p$, p is an integer number greater than or equal to 1, and $\alpha \ll n$, pieces of the imaging elements in the projected image of the grid pattern on the imaging elements, wherein the data producing section comprises an optical distortion calculating section that calculates an optical distortion amount generated at each section of the partial image data at the inspection position from Moire fringes appearing on the partial image data due to the grid pattern, and a noise reducing section that integrates the optical distortion amount in accordance with each section of the partial image data and produces data for inspection.

* * * * *